US007611413B2

(12) United States Patent
Ryan et al.

(10) Patent No.: US 7,611,413 B2
(45) Date of Patent: Nov. 3, 2009

(54) PINNING SYSTEM TO CONTROL PEOPLE

(75) Inventors: George William Ryan, Valencia, CA (US); Michael Wayne Odle, Santa Clarita, CA (US)

(73) Assignee: City of Los Angeles, Los Angeles, CA (US)

( * ) Notice: Subject to any disclaimer, the term of this patent is extended or adjusted under 35 U.S.C. 154(b) by 442 days.

(21) Appl. No.: 10/975,206

(22) Filed: Oct. 27, 2004

(65) Prior Publication Data

US 2006/0096599 A1    May 11, 2006

(51) Int. Cl.
*A63B 59/00*    (2006.01)
(52) U.S. Cl. ..................... 463/47.2; 119/801
(58) Field of Classification Search ................ 463/47.2, 463/47.4, 47.6; 119/801, 908; 135/65, 67, 135/70, 77, 78, 84
See application file for complete search history.

(56) References Cited

U.S. PATENT DOCUMENTS

| 1,945,430 | A | * | 1/1934 | Albert | 403/66 |
|---|---|---|---|---|---|
| 2,410,882 | A | * | 11/1946 | Lansden | 16/110.1 |
| 2,811,978 | A | * | 11/1957 | Russell | 135/65 |
| 3,125,287 | A | * | 3/1964 | Roehm | 231/2.1 |
| 3,341,235 | A | * | 9/1967 | Mattson et al. | 403/234 |
| 4,237,915 | A | * | 12/1980 | Zabielski et al. | 135/68 |
| 4,245,659 | A | * | 1/1981 | Shofner | 135/68 |
| 4,881,294 | A | * | 11/1989 | Riedl | 16/426 |
| 4,883,282 | A | * | 11/1989 | Wolf et al. | 280/43.24 |
| 5,378,156 | A | * | 1/1995 | Rohe | 434/253 |
| 5,460,373 | A | * | 10/1995 | McNutt | 463/47.2 |
| D365,695 | S | * | 1/1996 | Sibbitt, Sr. | D6/364 |
| 5,482,271 | A | * | 1/1996 | McNutt | 119/808 |
| 5,542,667 | A | * | 8/1996 | Lezdey et al. | 463/47.4 |
| 5,625,922 | A | * | 5/1997 | Morad | 16/426 |
| 5,893,799 | A | * | 4/1999 | Studley et al. | 463/47.2 |
| 6,135,888 | A | * | 10/2000 | Hindi | 463/47.2 |
| 7,029,397 | B1 | * | 4/2006 | Barwick | 463/47.4 |
| 7,047,990 | B2 | * | 5/2006 | Zambrano et al. | 135/82 |

* cited by examiner

*Primary Examiner*—William M Pierce
(74) *Attorney, Agent, or Firm*—Greenberg Traurig LLP

(57) ABSTRACT

A pinning system includes one or more pinning devices. A first elongated bar wherein one end of the first bar is for handling by an operator. The other end of the bar is for engagement of an individual. A head is located towards the end of the bar for engagement with the individual. In one pinning device, the head includes a hook, and the hook includes an elongated member for attachment to the first bar at a free end. The elongated member and free end are separated by a midsection such that the hook defines a substantially U-shaped member. In a second pinning device, an elongated bar includes a head located towards the end of the second bar for engagement with an individual. A mounting between the head and the end of the second bar permits the head to rotate relative to the bar. The head includes a relatively flat pad, and the pad is for engagement with the body of an individual.

11 Claims, 4 Drawing Sheets

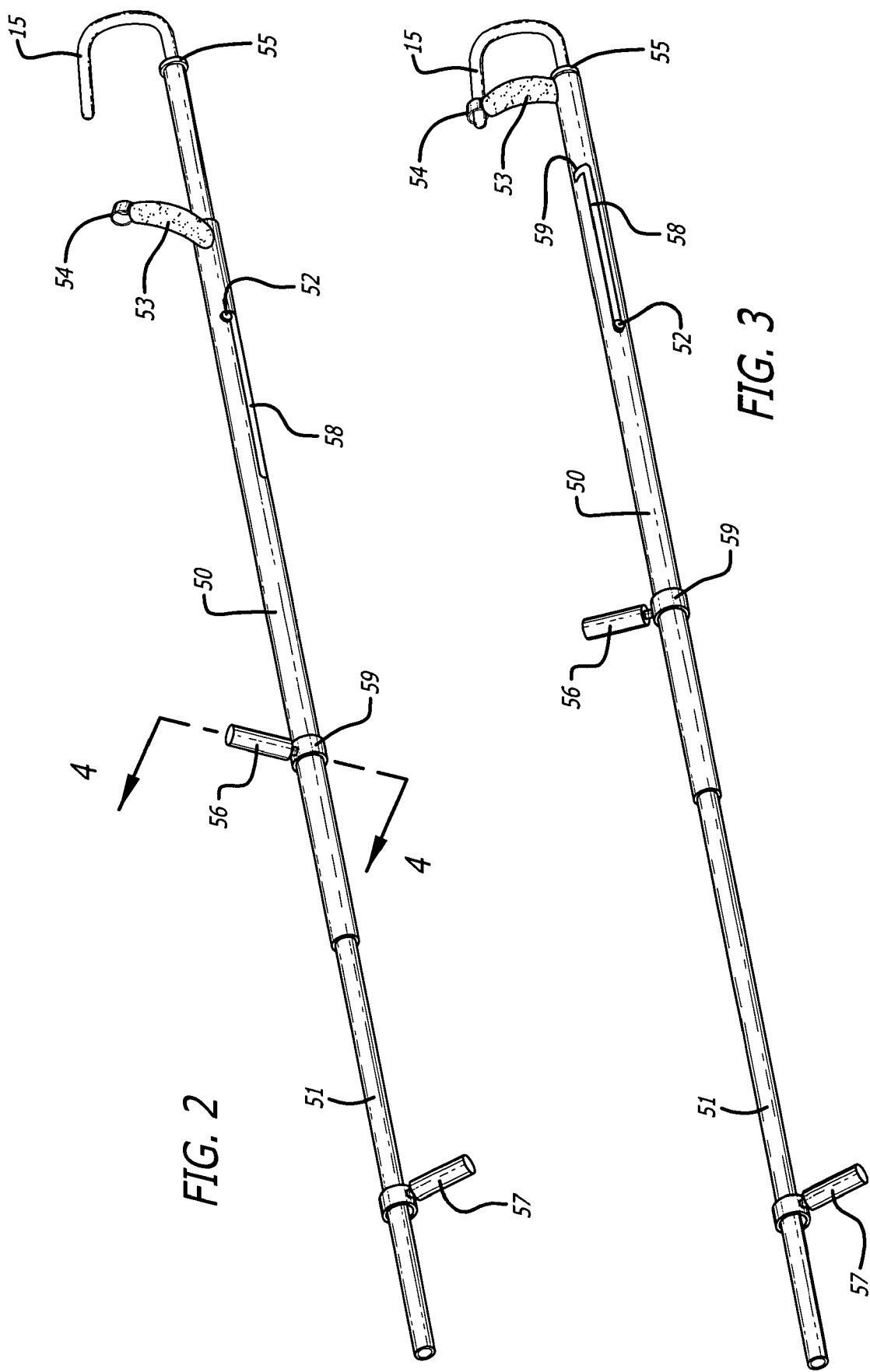

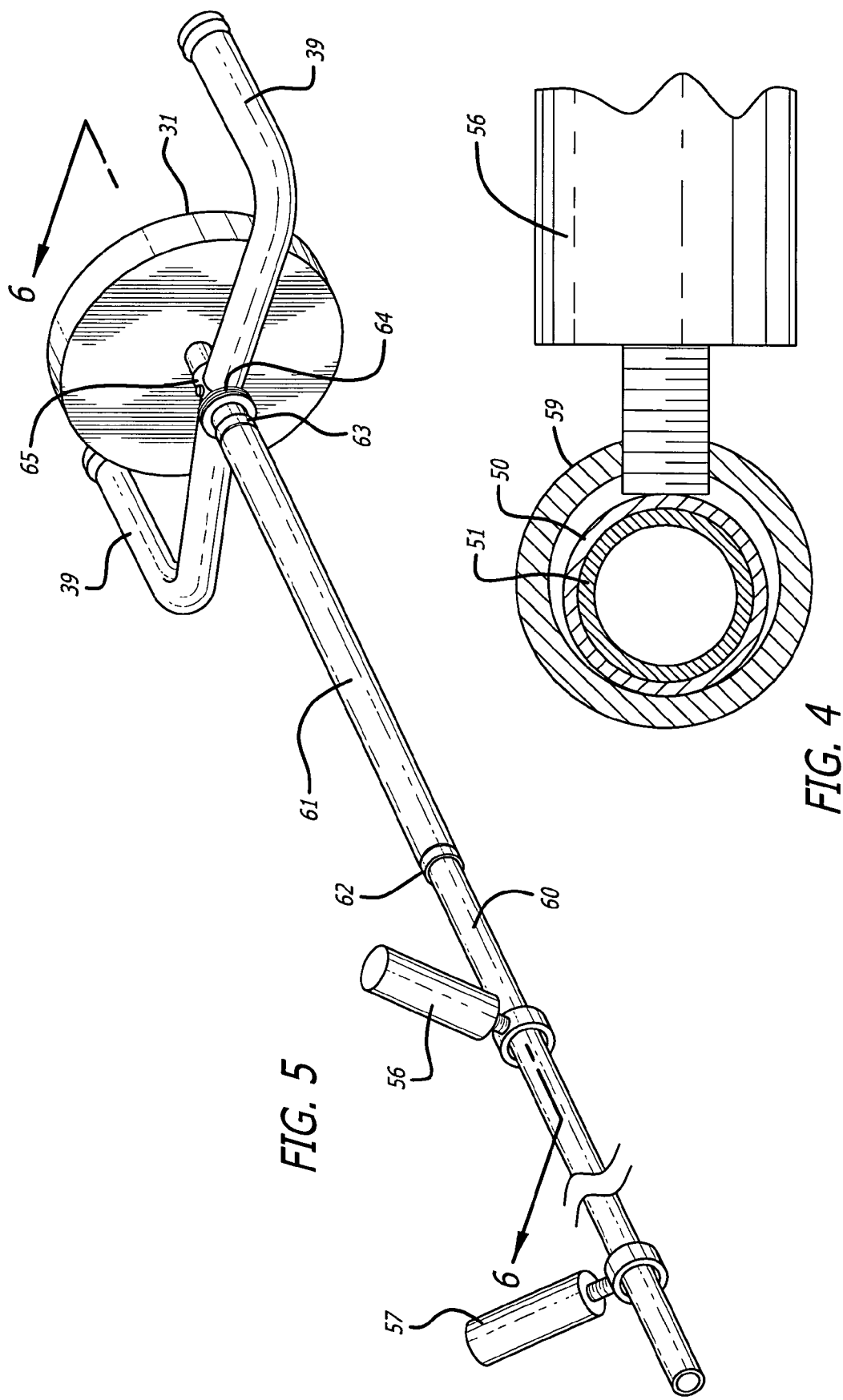

PINNING SYSTEM TO CONTROL PEOPLE

BACKGROUND

This disclosure relates to a pinning system, which uses one or more pinning devices for handling assailants.

There is a need to provide one or more devices that SWAT teams can use for securing assailants.

SUMMARY

A pinning system includes in one embodiment a pinning device in the nature of a hooking device. There is a first elongated bar wherein one end of the first bar, is for handling by an operator. The other end of the bar is for engagement of an individual. A head is located towards the end of the bar for engagement with the individual. The head includes a hook, and the hook includes an elongated member for attachment to the first bar at a free end. The elongated member and free end are separated by a midsection such that the hook defines a substantially U-shaped member.

There can be a closure member to operate with the U-shaped member so that a limb such as the lower portion of the leg of an assailant can be effectively trapped between the U-shaped member and the closure member.

A pinning system includes in a second embodiment of a pinning pole. There is a second elongated bar having a head located towards the end of the second bar for engagement with an individual. A mounting between the head and the end of the second bar permits the coaxial tubes formed in the front of the elongated bar to rotate relative to the bar. The head includes a relatively flat pad, and the pad is for engagement with the body of an individual.

In one embodiment of the disclosure, the pinning pole includes a padded U-shaped retention device. The construction of coaxial tube of the elongated bar and handles of the elongated bar is such that it is less likely to be subjected to torque action if an assailant moves the U-shaped retention device. An individual can hold the bar securely as an assailant tries to move or turn the U-shaped retention device. In a second embodiment of the disclosure, there is a flat second striking pad.

There is one or more swivel or coaxial sleeves located around and/or towards one end of the elongated bar pole and one or more adjustable handles to facilitate manipulation of the first and/or second pinning devices of the pinning system on the other end.

The pinning system can use one or more of the pinning devices in an operation to subdue an assailant.

The disclosure is further described with reference to the accompanying drawings.

DRAWINGS

FIG. 2 is a first view of a first pinning device in a first position.

FIG. 3 is a second view of a first pinning device in a second position.

FIG. 4 is a fragmental cross-sectional view of the handle for one or more of the pinning devices.

FIG. 5 is a view of the second pinning device.

DESCRIPTION

Figure 1:
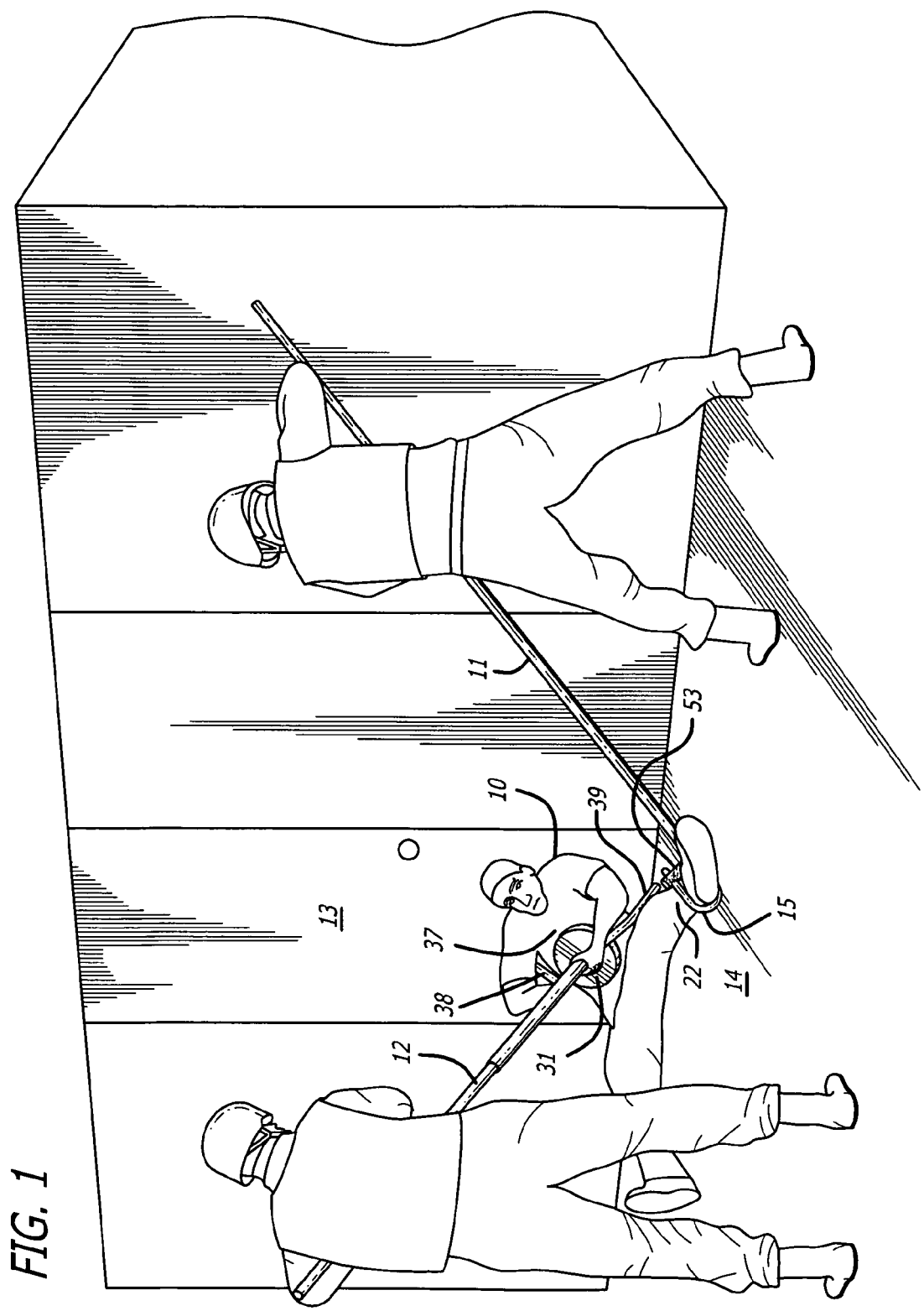
FIG. 1 is a representation of an assailant being secured by two pinning devices of the pinning system.

A pinning system includes two different pining devices.

In both embodiments of the first pinning device, each device comprises an elongated bar wherein one end of the bar is for handling by an operator and the other end of the bar is for engagement of an individual.

In the embodiments, there is a head located towards the end of the bar for engagement with an individual. A mounting between the head and the end of the bar fixes the head relative to the bar. There is an elongated bar wherein one end of the bar is for handling by an operator and the other end of the bar is for engagement of an individual.

In a first embodiment, the head includes a hook, and the hook includes an elongated member for attachment to the bar and an end, the elongated member and free end being separated by a midsection such that the hook defines a substantially U-shaped hook member.

In this first embodiment, the head includes the hook, and the hook includes an elongated member for attachment to or closure with the first elongated bar and a free end.

There is a stop mounted on the elongated bar. The stop is movable relative to the free end of the hook thereby to effect closure of the mouth of the hook when the stop is located in adjacency with the free end. The stop is movable axially relative to the elongated bar.

There is a handle for the elongated bar, the handle being operable by the operator to permit closure of the hook at the end remote from the operator. There can be movement relatively about an axis through the elongated bar. The handle for the elongated bar is operable by the operator to permit movement of a stop member relative to a hook at the end remote from the operator. The movement is selectively at least one of axial or rotation relative to the elongated bar.

In another aspect, the pinning device in a second embodiment of the pinning system includes a head. A head is located towards the end of the second bar for engagement with an individual. The head includes a relatively flat pad for engagement with the body of an individual. A mounting for the pad and the elongated bar permits the pad to be secured relative to the axis of the elongated bar.

A fork member is adjacent the pad. The fork member includes tines to either side of the pad. The fork member is mounted with a flexible mounting such that the tines of the fork are relatively fixed in relation to the elongated bar.

The pinning system is described with reference to each of the pinning devices. An assailant 10 is shown secured by a first pinning device 12 and a second pinning device 11. The assailant 10 is trapped against a gate 13 and a floor 14.

As illustrated in FIG. 1, the exemplary system in one form can operate by using the pinning device to help control the assailant 10 while the other officer uses the ankle grab device to grab the ankle and pull the subject to the ground.

FIG. 2 shows the ankle grab device. There are two main pieces part 50 and part 51. Part 50 slides independently along the longitudinal axes of part 51. Retention is affected by bolt 52 that slides in a groove 58. The groove 58 has a hook element 15 at one end as illustrated in FIG. 3.

This retains tube 50 so that it cannot move when the user is getting ready to capture the assailant's ankle. In FIG. 2 it is shown in an open state and bolt 52 is in the small notch at the end of groove 58, which does not allow it to slide back and forth. Rotation up to 90 degrees is possible so that the top of hook 15 is free, at which point the officer would use handles 56 and 57 to hold and support the overall apparatus. Handle 56 would be then used once the hook 15 is around the ankle of the suspect to rotate counterclockwise and then push forward, taking part 54 and locating it and locking it at the end of hook 15 where the pad 53 would then be capturing the top of the ankle and not allowing it to move.

Part 50 slides down this shaft in the direction of the slot 58 or bolt 52 and comes to a dead stop at the end of the slot. A stop 55 at the end ensures that if the bolt were to shear off or something were to happen, one could not compress the hook element 53 into 15 any further, possibly breaking the ankle. Stop 55 also acts as a secondary stop.

Handles 56 and 57 are similar in outer appearance. Handle 56 in FIG. 2 has a cross section 44 through it, which is illustrated in FIG. 4. There is one position where it is used to lock both the pole elements 50 and 51 by compressing them together to not allow part 53 or the entire slide 50 to slide back and forth. Once the officer slides the handle forward, sliding 50 down and capturing the ankle, pressure in the twisting motion to the handle 56 is applied, which through the screw threads of part 59 of the screw threads of the handle 56, is threaded into part 59. This exerts more force into that area, locking those two tubes 50 and 51 together and not allowing them to slide.

Figure 6:
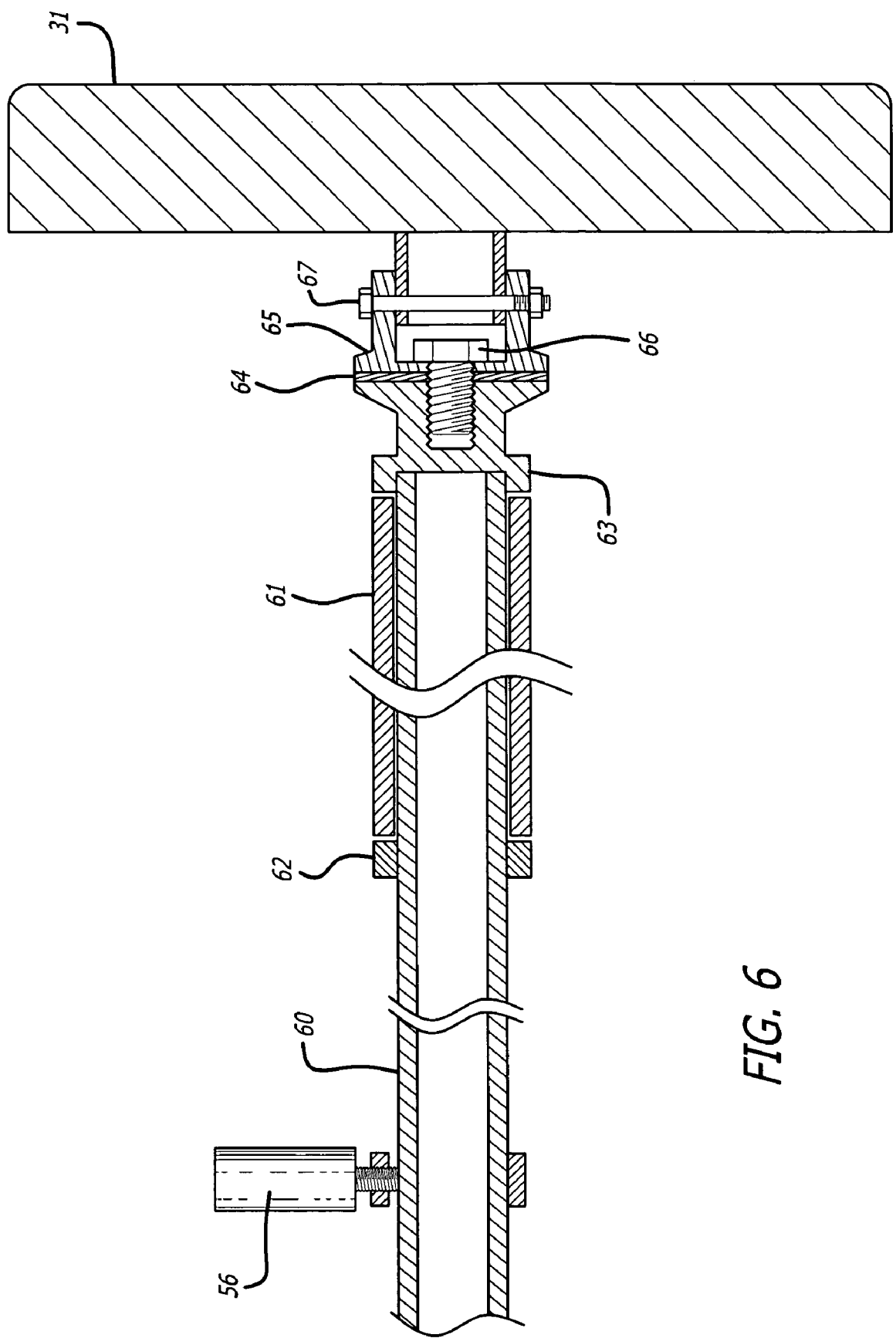
FIG. 6 is a fragmental cross-sectional view of the pad securing mechanism of the second pinning device.

In other views, such as in FIG. 6, that handle 56 simply acts just as a handle and is secured to the single pole. It is not the double pole arrangement for locking it in place.

The pinning device is shown in FIG. 5. There are the same handles 56 and 57 though they are secured to pole 60. Pole 60 slides all the way forward and is secured in the coupling device 63. There is attached at the end, a pad 31, which will go up against the chest or torso area of the assailant as well as it has the arms 39 on both sides that are permanently affixed to a part that will be later seen as part 65 in FIG. 6.

Part 61 in FIG. 5 is rotatable so that if the assailant grabs part 61 he cannot exert any force other than through the center line of the pole, any twisting motion and part 61 will freely rotate. This is also a feature of the arms 39. These arms rotate if they are grabbed. FIG. 5 has a cross section taken through the centerline 6-6 that shows more detail.

In FIG. 6 the cross section on the left shows handle 56 secured to part 60, which is the main pole of the device. Part 61 is the rotational piece and it is illustrated in a foreshortened manner. Part 62 is a stop that would be welded or secured in some way to part 60. Part 63 is the other stop device for 61, so it allows it to rotate. 63 also acts as a receptacle for bolt 66 to be able to bolt the subassembly 65 to 63. When bolt 66 is bolted to 63, there is a bushing 64 that is inserted between the two pieces 63 and 65. This allows the free rotation of the whole pad assembly 65 and 31 as bolt 67 secures the two together. Bolt 66 locks down to a point where it does not completely lock down and part 64 acts as a bushing to be able to have free rotation between the parts. This shows that rotation that 57 described in FIG. 5 of part 39 and 31 as well as the rotation of the piece 61.

Many other forms of the disclosure exist, each differing from the other in matters of detail only. For instance, instead of a circular pad this can be a different shaped pad. The fork member may have a different number of tines. In some cases there may be less or no mobility between the components relative to the elongated bar. In other variations, there may be axial movement and no rotational movement or rotational movement and no axial movement. The shape of the hook can vary and may be angled differently relative to the elongated bar. A different number of handle devices can be used at the opposite end of the bar and the handle devices can be different shaped. The elongated bars can in some forms be approximately 8 feet in length, but there can be other forms where the bar is shorter or longer. In use, the pad member would be used first, and then the hook member.

The invention is to be determined solely by the following claims.

The invention claimed is:

1. A pinning device comprising:
    an elongated bar having a first end for handling by an operator and a second end for engagement of an individual;
    two separate handles connected to the elongated bar near the first end of the bar, the two separate handles extending radially from the elongated bar;
    a head located on the second end of the bar, the head including a pad having a relatively flat bottom surface; and
    two arms connected to the elongated bar near the second end of the bar, the two arms forming a fork member longitudinal to the elongated bar and extending longitudinally past the bottom surface of the pad.

2. The pinning device of claim 1 further including a mounting for the pad and the elongated bar wherein the pad is fixed relative to the elongated bar.

3. The pinning device of claim 1 wherein the fork member is independently rotatable with respect to the elongated bar and the head, the fork member independently rotatable along a longitudinal axis defined by the elongated bar.

4. The pinning device of claim 1 further including a hollow cylinder encircling a section near the second end of the elongated bar, the elongated bar passing through the hollow cylinder such that the hollow cylinder is independently rotatable with respect to the elongated bar and the head, and a stop on the elongated bar to prevent the hollow cylinder from sliding towards the first end of the bar.

5. The pinning device of claim 1 wherein the two separate handles form an angle with each other less than 180°.

6. The pinning device of claim 1 wherein the two arms extend radially from the elongated bar and extend past the pad in a direction parallel to a longitudinal axis defined by the elongated bar.

7. A pinning device comprising:
    an elongated bar having a first end for handling by an operator and a second end for engagement of an individual;
    two separate handles connected to the elongated bar near the first end of the bar, the two separate handles extending radially from the elongated bar;
    two arms connected to the elongated bar near the second end of the bar, the two arms forming a fork member longitudinal to the elongated bar;
    a hollow cylinder encircling a section of the elongated bar near the two arms, the elongated bar passing through the hollow cylinder such that the hollow cylinder is independently rotatable with respect to the elongated bar and the two arms; and
    a stop on the elongated bar to prevent the hollow cylinder from sliding towards the first end of the bar.

8. The pinning device of claim 7 wherein the fork member is independently rotatable with respect to the elongated bar, the fork member independently rotatable along a longitudinal axis defined by the elongated bar.

9. The pinning device of claim 7 further including a pad located on the second end of the elongated bar, the pad attached to the elongated bar but not attached to any of the arms.

10. The pinning device of claim 7 wherein the two separate handles form an angle with each other less than 180°.

11. The pinning device of claim 9 wherein the two arms extend radially from the elongated bar and extend past the pad in a direction parallel to a longitudinal axis defined by the elongated bar.

* * * * *